(12) United States Patent
Strauss et al.

(10) Patent No.: US 8,162,991 B2
(45) Date of Patent: Apr. 24, 2012

(54) MULTI-PLANAR, TAPER LOCK SCREW

(75) Inventors: Kevin R. Strauss, Columbia, MD (US);
Michael Barrus, Asburn, VA (US);
Scott A. Jones, McMurray, PA (US)

(73) Assignee: K2M, Inc., Leesburg, VA (US)

( * ) Notice: Subject to any disclaimer, the term of this patent is extended or adjusted under 35 U.S.C. 154(b) by 1280 days.

(21) Appl. No.: 11/493,625

(22) Filed: Jul. 27, 2006

(65) Prior Publication Data
US 2008/0027432 A1   Jan. 31, 2008

(51) Int. Cl.
*A61B 17/70* (2006.01)

(52) U.S. Cl. ........................................... 606/269

(58) Field of Classification Search ........... 606/264–275
See application file for complete search history.

(56) References Cited

U.S. PATENT DOCUMENTS

| | | | |
|---|---|---|---|
| 4,946,458 A | | 8/1990 | Harms et al. |
| 5,304,179 A | | 4/1994 | Wagner |
| 5,672,176 A | | 9/1997 | Biedermann et al. |
| 5,683,392 A | * | 11/1997 | Richelsoph et al. ......... 606/272 |
| 5,728,098 A | | 3/1998 | Sherman et al. |
| 6,248,105 B1 | | 6/2001 | Schlapfer et al. |
| 6,355,040 B1 | | 3/2002 | Richelsoph et al. |
| 7,090,674 B2 | | 8/2006 | Doubler et al. |
| 2005/0096653 A1 | * | 5/2005 | Doubler et al. ............ 606/61 |
| 2006/0276792 A1 | | 12/2006 | Ensign et al. |
| 2008/0243193 A1 | | 10/2008 | Ensign et al. |

FOREIGN PATENT DOCUMENTS

| | | |
|---|---|---|
| WO | WO97/14368 | 4/1997 |
| WO | WO2004/089245 | 10/2004 |
| WO | WO2005/041821 | 5/2005 |

OTHER PUBLICATIONS

Supplementary European Search Report, issued Sep. 11, 2009, 3 pages.
International Search Report from International Appl. No. PCT/US06/29225, dated May 20, 2008, 2 pages.
Written Opinion of the International Searching Authority from International Appl. No. PCT/US06/29225, dated May 20, 2008, 3 pages.

* cited by examiner

*Primary Examiner* — Thomas C. Barrett
*Assistant Examiner* — David Bates
(74) *Attorney, Agent, or Firm* — Carter, DeLuca, Farrell & Schmidt, LLP

(57) ABSTRACT

Provided is a novel multi-planar taper lock screw for connecting a connecting rod to bone. The screw is capable of multi-directional articulation while the connecting rod position can remain stable and aligned as needed. After the screw had been articulated and properly positioned, it can be locked such that the screw and the connecting rod will remain in relative position to the bone. The screw is configured for easy insertion and connection as well as easy removal and disconnection from the connecting rod. Also provided is a system for fixing two or more bones or bone fragments and a kit for fixing bones or bone fragments. A method of fixing bones or bone fragments is also provided.

20 Claims, 4 Drawing Sheets

MULTI-PLANAR, TAPER LOCK SCREW

BACKGROUND OF THE INVENTION

1. Field of the Invention

The present invention relates to orthopedic surgery, and in particular to devices and prosthesis for stabilizing and fixing the bones and joints of the body. Particularly, the present invention relates to a multi-planar, taper lock screw for securing a spinal rod to a vertebra, wherein the screw can be easily inserted into a vertebra and connect to a spinal rod that can be connected to other vertebrae not on the same plane and can provide a structural configuration that facilitates ease of insertion or removal of the screw as desired. More particularly, the present invention relates to a novel multi-planar, taper lock screw having a proximal flange that is easily accessible to facilitate the connection of a complementarity configured gripping tool for improved ease of locking and unlocking of the screw when desired.

2. Background of the Technology

It is a common surgical requirement to stabilize and fix bones and bone fragments in a particular spatial relationship to correct the location of skeletal components due to injury or disease. This can be accomplished by using a number of bone pins, anchors, or screws placed in bones across a discontinuity in the bone or bone fragments, such as a fracture, or adjacent vertebrae, or a joint, connected by a rod to maintain a predetermined spatial location of the bones or bone fragments. In some cases the use of these devices may be permanently implanted in the subject. In other cases, the devices may be implanted only as a temporary means of stabilizing or fixing the bones or bone fragments, with subsequent removal when no longer needed. It is also common that device implants that were intended to be permanent may require subsequent procedures or revisions as the dynamics of the subject's condition warrant. For these reasons, it is desirable that an implanted device be provided, which can be easily locked and unlocked as desired by the surgeon.

Spinal fixation apparatuses are widely employed in surgical processes for correcting spinal injuries and diseases. These apparatuses commonly employ longitudinal link rods secured to the bone such as vertebrae by spinal bone fixation fasteners such as pedicle screws, hooks and others.

Many conventional devices for locking a spinal rod to a fixation hook or screw do not offer the needed variability to allow the spinal rod to be easily connected to adjacent vertebrae, which are not aligned on the same plane. Some effort has been made to provide a multi-planar screw; however, even for devices that have attempted to address the issue of securing rods to differently aligned vertebrae, there remains the problem of providing such a multi-planar screw that can also be easily locked and unlocked.

To meet the problem of securely connecting adjacent vertebrae, not on a common plane a requirement exists to provide a multi-planar, taper lock screw that can be easily inserted and easily removed from the vertebral bone as desired. It is also desirable that such a screw be configured so that it can be locked into position in relation to the bone and the spinal rod without the need to exert any additional torque to the device or force on the patient. Additionally, such a multi-planar screw that can be used without the need for an additional locking piece, such as a set screw or the need to thread a locking device into place would be desirable.

Conventional efforts to meet this need have fallen short in that no spinal screw has been provided that adapts the spinal rod to the multi-planar environment of the spine while providing a screw head configuration that presents ease of locking and unlocking the rod to the screw.

Thus a need exists for a multi-planar, taper lock screw that also provides a screw head configuration that is easily grasped by a complementary tool used by an operator for locking and unlocking the rod and screw.

SUMMARY OF THE INVENTION

The multi-planar taper lock screw having a proximal flange provides a novel multi-planar screw for connection of a spinal rod to a first vertebra wherein the head of the screw is easily connected to a rod that can also be connected to an adjacent vertebra not in the same plane as the first vertebra and, due to a novel configuration of the head, can also be easily grasped by an operator using a complementary grasping tool to remove the screw when desired.

Also provided is a novel multi-planar taper lock screw configured to be easily connected to the vertebra and then connected to a spinal rod without the additional application of torque.

Also provided is a novel multi-planar taper lock screw configured to have a slidable outer housing over an inner housing containing a spherically configured, pivotable screw head and a removable spinal rod wherein the outer housing can be selectively positioned to fully lock the screw head and the spinal rod in position within the inner housing.

Also provided is a novel multi-planar taper lock screw configured to have a slidable outer housing over an inner housing containing a spherically configured, pivotable screw head and a removable spinal rod wherein the outer housing can be selectively positioned to fully lock the screw head and the spinal rod in position within the inner housing or can be selectively positioned to lock only the screw head in position while permitting a sliding and rotating motion of the spinal rod about its long axis within the inner housing.

Also provided is a kit that can include at least two of the novel multi-planar taper lock screws, at least one rod device, and surgical instruments having a configuration complementary to the configuration of the head of the novel screw and configured to facilitate grasping of the screw head for locking and unlocking of the rod.

Also provided is a method of using the novel multi-planar taper screw wherein the surgical procedure employed, in comparison to conventional methods, is quickly accomplished for locking or unlocking of the device.

BRIEF DESCRIPTION OF THE DRAWINGS

The foregoing and other features of the present invention will become apparent to one skilled in the art to which the present invention relates upon consideration of the following description of the invention with reference to the accompanying drawings, wherein.

DETAILED DESCRIPTION OF THE INVENTION

Detailed embodiments of the present invention are disclosed herein; however, it is understood that the following description is provided as being exemplary of the invention, which may be embodied in various forms without departing from the scope of the claimed invention. Thus, the specific structural and functional details provided in the description are non-limiting, but serve merely as a basis for the invention defined by the claims provided herewith.

Figure 1:
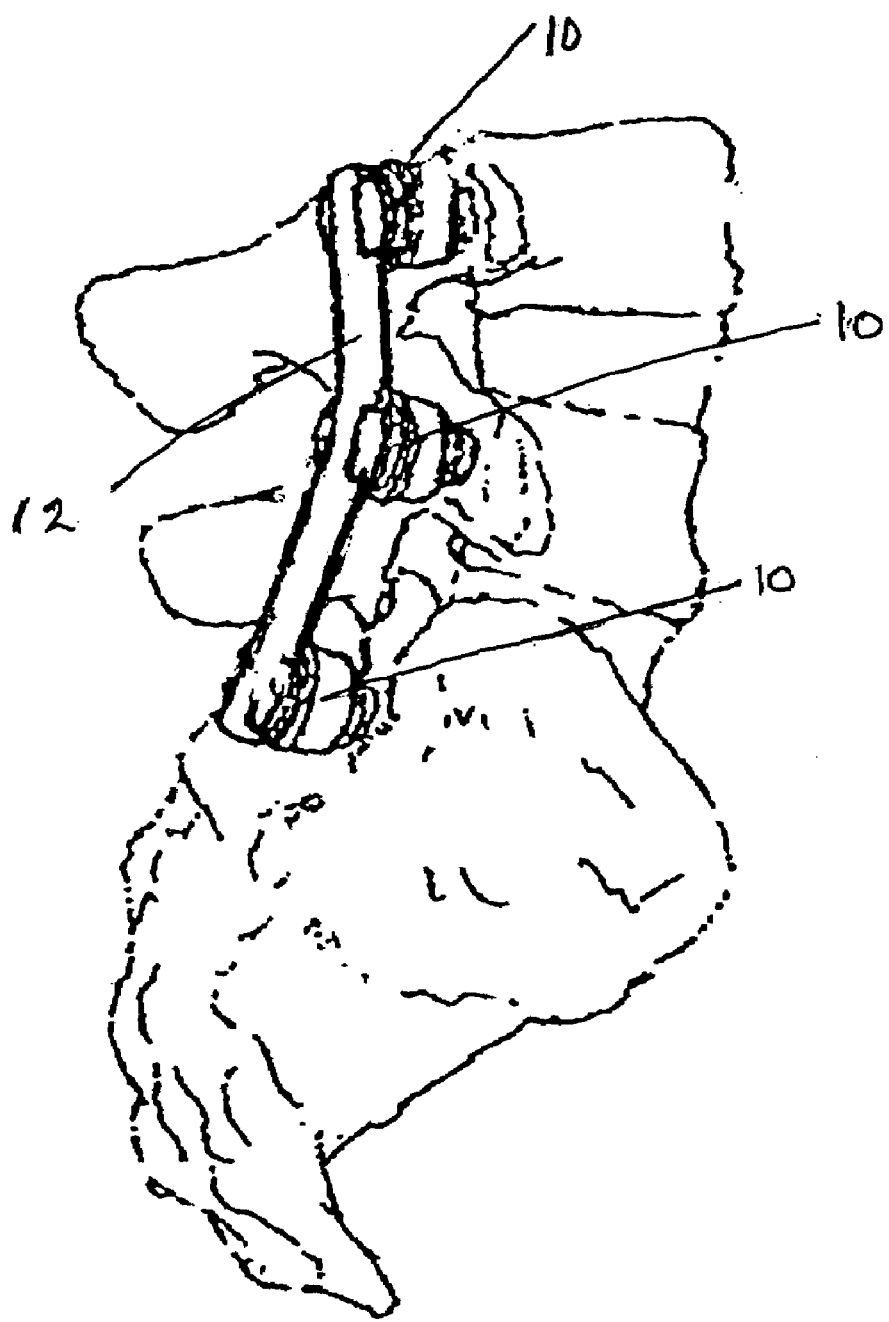
FIG. 1 shows a side view of a surgical rod using the present invention to connect in sequence to three adjacent bone structures of the spine, each bone structure being aligned with a different plane.
Figure 2:
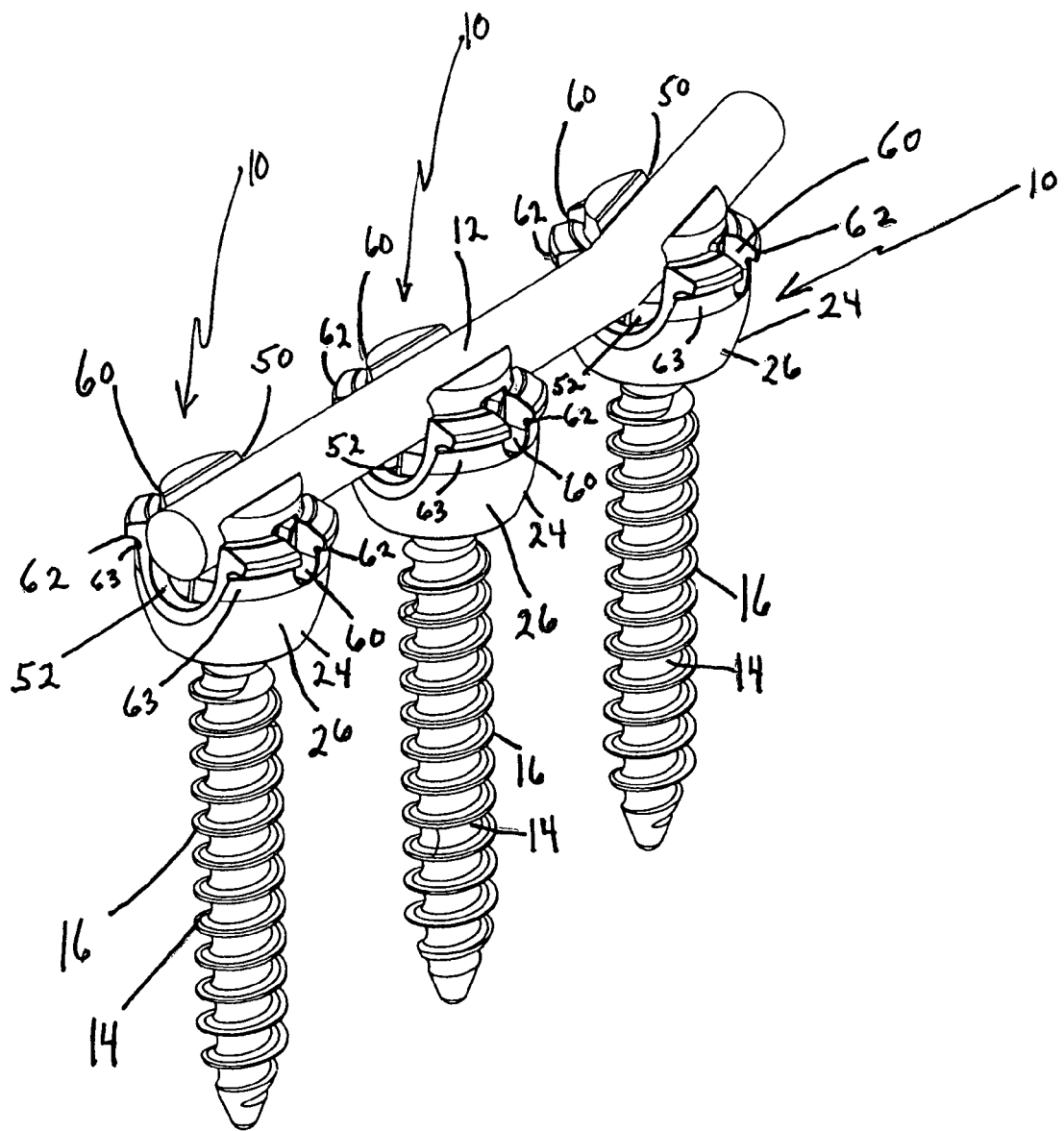
FIG. 2 shows a perspective view of a surgical rod connected to three screws according to the present invention.

As shown in FIGS. 1-4B, a novel multi-planar tapered lock screw 10 is so configured so as to facilitate ease of insertion of the screw 10 into bone and connection to surgical devices such as spinal rods as well as facilitating easy locking and unlocking as desired. FIG. 1 illustrates a portion of the lumbar spine with an example of a unilateral orthopedic fixation assembly that includes a connecting rod 12 and three screws 10 according to the present invention. In the example shown, the connecting rod 12 is a spinal rod having a generally circular cross section; however, it is within the concept of the invention to secure connecting rods of any suitable cross-sectional configuration required for the need at hand.

As best shown in FIGS. 2, 3A-B, and 4A-B, the multi-planar tapered locking screw 10 of the present invention includes a screw shaft 14, which defines an external helical thread 16 for penetrating cancellous bone through the application of torque. The upper portion of the screw shaft 14 terminates in a screw head 18, that is generally spherical in part and at its uppermost surface 20 defines a screw head recess 22, which has a recess surface configuration that is complementary to the shape of a tightening and/or loosening tool. Without departing from the concept of the present invention, the screw head recess 22 can also be configured as a protrusion rather than a recess provided that the protrusion has a surface that is complementary for gripping attachment to a tool for tightening and/or loosening and provided that the height of the protrusion above the uppermost surface 20 of the screw head 18 is not such that it obstructs or interferes with any of the functions of the screw 10.

As best shown in FIG. 1, the screw 10 of the present invention is capable of connecting a connecting rod 12 to multiple vertebrae, which are aligned in the spinal column on different planes due to the natural curvature of the spine, by the use of a dual layered screw housing 24 that includes an outer housing 26 and an inner housing 28. The outer housing 26 is configured such that at least a portion of the inner surface 30 of the outer housing 26 is capable of selectively sliding over a portion of the outer surface 32 of the inner housing 28 in an upward and downward direction along the longitudinal axis of the screw 10. The configuration of both the outer housing 26 and the inner housing 28 are complementary in that when the outer housing is slid downward in relation to the inner housing at least one outer housing internal compression contact surface 34 is brought to bear against at least a portion of the outer wall 36 of the inner housing 28 and by that compressive force causes the inner housing 28 to in turn to mechanically transmit that compressive force inward toward the central longitudinal axis of the screw 10.

A screw head articulation recess 38 is defined in the interior of the lower portion 40 of the inner housing 28. The interior surface 42 of the articulation recess 38 has a complementary surface configuration to the generally spherical shape of the screw head 18 so as to facilitate multi-planar rotational articulation of the screw head 18 within the recess 38. The lower most portion of the inner housing 28 defines a screw shaft exit portal 44, that is sized small enough retain the spherical screw head 18 within the recess 38 but is large enough to allow multi-directional movement of the screw shaft that extends exterior to the inner housing 28. The recess 38 can include a recess upper edge 46 that is configured to selectively exert a locking compressive force against the screw head 18. A recess lower edge 48 can also be provided for the same purpose. It is also within the scope of the present invention that all or portions of the interior wall of the recess 38 can selectively provide the compressive force against the screw head 18 that is sufficient to hold the screw head in a locked position.

The upper portion of the inner housing 28 defines an inner housing connecting rod slot 50 that is sized and configured to permit a connecting rod 12 to be placed transversely within the upper portion of the inner housing 28. An outer housing connecting rod slot 52 can be provided that is in common alignment with the inner housing connecting rod slot but is not necessarily of exactly the same measurement as the inner housing slot 50. The inner housing connecting rod slot 50 can define at least one compression contact surface 54 that when forced into compressive contact with a connecting rod 12 present in the slot 50, the contact surface can serve to securely hold the rod 12 in its relative position to the inner housing 28. Preferably the inner housing connecting rod slot 50 is provided with an opposing upper compression contact surface 56 and an opposing lower compression contact surface 58, which together can selectively be forced against the connecting rod 12 so as to secure and releasably lock it in place within the inner housing 28.

Figure 3A:
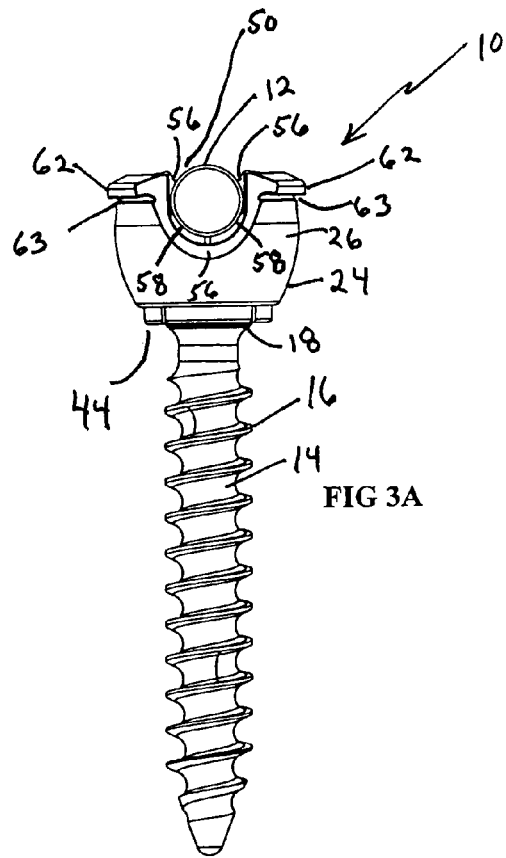
FIG. 3A shows a side view of the screw according to the present invention, the screw being configured in a closed position; that is with a surgical rod secured and locked in the screw body.
Figure 3B:
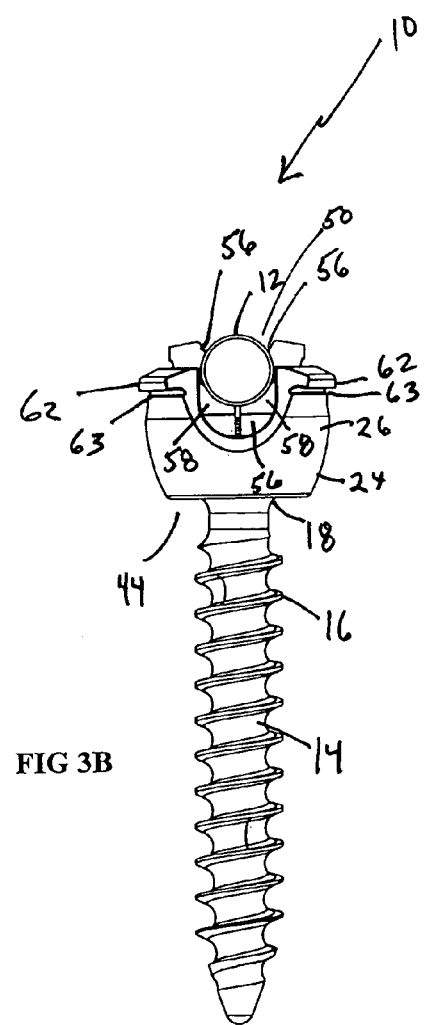
FIG. 3B shows a side view of the screw according to the present invention, the screw being configured in an open position, that is with a surgical rod in place within the screw but not secured thereto.
Figure 4A:
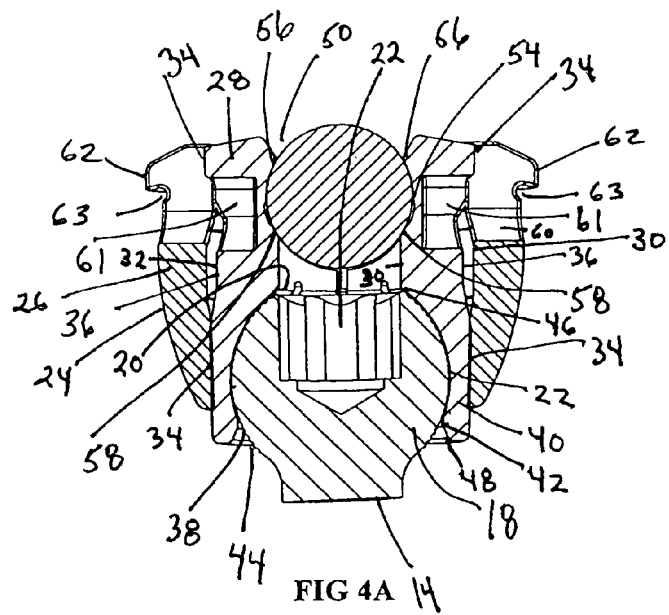
FIG. 4A shows a cross-sectional view of the body portion of the screw of the present invention in a closed position, that is with a surgical rod secured and locked in the screw body.
Figure 4B:
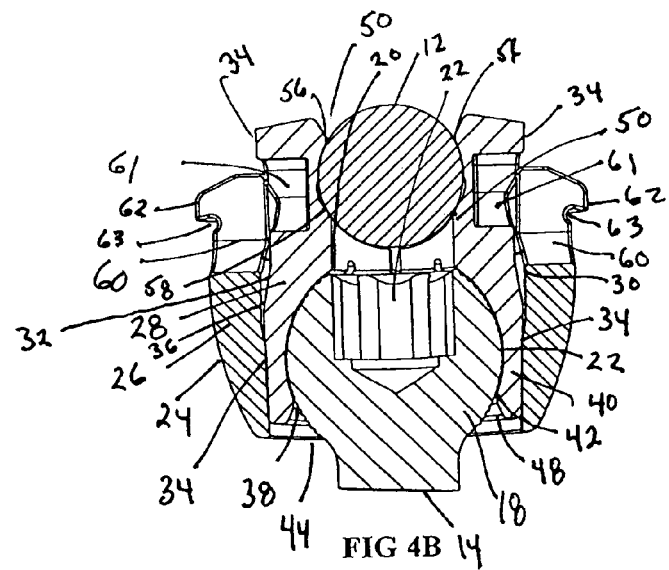
FIG. 4B shows a cross-sectional view of the body portion of the screw of the present invention in an open position, that is with a surgical rod in place within the screw body but not secured thereto.

Preliminary to operation of the screw 10, the outer housing 26 should be positioned in the open position; that is it should be slid downward relative to the inner housing 28. The screw shaft 14 can then be driven into the cancellous bone by providing torsional force via a tool configured to mate with and grip the screw head recess 22. After the screw shaft 14 is positioned within the bone and the driving tool removed from the screw 10, a connecting rod 12 can be positioned transversely along the common course of and within the inner housing connecting rod slot 50 and the outer housing connecting rod slot 52. Upon completion of all manipulation of the connecting rod 12 that may be required to articulate the screw head 18 within the inner housing recess 38 and the connecting rod 12 within the inner housing connecting rod slot 50, the outer housing 26 can be grasped by the operator using a complementarity configured grasping tool that when activated slides the outer housing 26 upward circumferentially over the outer surface of the inner housing 28 from the open or unlocked position to the closed or locked position, as best shown in FIGS. 3A and 4A. Similarly, the operator can use a complementarity configured unlocking tool to grasp the inner housing 28 and slidably move the outer housing downward along the outer surface of the inner housing 28 from a closed or locked position to an open or unlocked position, as best shown in FIGS. 3B and 4B. The screw 10 can be provided with an inner housing access slot 60 defined through the wall of the outer housing 26, which provides access for the unlocking tool that is designed to make grasping contact with an inner housing tool receptor 61 to facilitate quickly unlocking the screw 10 and permit movement of the screw head 18 within the articulation recess 38 and removal of the connecting rod 12 from the inner housing connecting rod slot 50. The outer housing can be provided with a tool receiving element for the operator's tool, which is preferably a proximally located annular flange 62 or circumferentially defined annular gripping groove 63, as best shown in FIGS. 2, 3A-B, and 4A-B.

It is within the concept of the invention to selectively position the outer housing 26 along the surface of the inner housing 28 such that the compressive force exerted by the outer housing 26 on the inner housing 28 is such that a partial lock position can be attained; that is, by a limited sliding movement of the outer housing 26, compressive pressure will be exerted only on the articulation recess and the screw head 18 contained therein while the connecting rod 12 will remain free to slide transversely within the inner housing connecting rod slot 50. Using this partial lock of the screw 10, the operator can first position the screw 10 relative to the bone into which the screw shaft 14 has been attached and then manipulate the connecting rod 12 within the screw 10 to optimize its position before sliding the outer housing 26 into a full locked position on the inner housing 28.

The materials used to construct the present invention are those which have sufficient strength, resiliency, and biocompatibility as is well known in the art for such devices. Methods of manufacture of such surgical implant devices is also well known in the art.

It is within the concept of the present invention to provide the multi-planar taper lock screw 10 as part of a kit for use in a surgical process, the kit comprising at least two of the screws 10 and at least some of the associated tools for using the screws to connect a surgical rod to adjacent bones or bone fragments. In addition, the kit can contain surgical rods, such as, for example, spinal rods. Additional devices such as cross-connectors or links can also be included in the kit.

Each of the embodiments described above are provided for illustrative purposes only and it is within the concept of the present invention to include modifications and varying configurations without departing from the scope of the invention that is limited only by the claims included herewith.

What is claimed is:

1. A multi-planar taper lock screw as a connecting device for securing a connecting rod to bone, comprising:
    an inner housing defining a longitudinal axis;
    an outer housing being slidable relative to said inner housing along said longitudinal axis and including a proximally located annular flange extending therefrom, said annular flange being generally transverse to said longitudinal axis, said annular flange being positioned to overhang a circumferentially defined annular gripping groove, said gripping groove being configured to facilitate grasping contact of a grasping tool for facilitating locking of a screw, said gripping groove projecting radially inwardly from at least a portion of a circumference of said outer housing;
    said screw including a threaded shaft and a head, said head disposed in said inner housing and positioned for angular movement relative to said longitudinal axis of said inner housing;
    a first slot defined in said inner housing and being positionable between a first position, where said first slot releasably locks a connecting rod therein, and a second position, where said connecting rod is freely positionable into and out of said first slot, said connecting rod defining a central longitudinal axis perpendicular to said longitudinal axis of said inner housing; and
    a second slot defined in said outer housing and being aligned with said first slot in at least one of said first and second positions;
    said inner housing and said outer housing having generally complementary tapered opposing surfaces such that said outer housing applies a compressive force onto said inner housing as said outer housing slides proximally, said compressive force being sufficient to compress said inner housing to maintain said connecting rod and said screw in a releasably fixed position relative to said inner housing when said outer housing is in a proximal-most position;
    at least a portion of said outer housing intersects a plane extending laterally from said central longitudinal axis of said connecting rod as said outer housing slides relative to said inner housing along said longitudinal axis.

2. The multi-planar taper lock screw of claim 1, wherein said flange defines a recess for engaging a portion of a tool.

3. The multi-planar taper lock screw of claim 1, wherein at least one of the first and second slots is perpendicular to the longitudinal axis.

4. The multi-planar taper lock screw of claim 1, wherein said flange extends radially outward and downward from at least a portion of a circumference of said outer housing.

5. A multi-planar taper lock screw as a connecting device for securing a connecting rod to bone, comprising:
    a screw inner housing and a screw outer housing, said screw outer housing being circumferentially disposed around at least a portion of said inner housing and being sized and configured to be capable of slidable movement along a common longitudinal axis of said inner housing and outer housing;
    said screw outer housing including a proximally located annular flange projecting radially outward from at least a portion of a circumference of said outer housing, said annular flange being positioned and configured to be accessed and grasped by a grasping tool for facilitating locking of a screw, said annular flange being positioned to overhang a circumferentially defined annular gripping groove, said gripping groove being configured to facilitate grasping contact of said grasping tool for facilitating locking of said screw, said gripping groove projecting radially inwardly from at least a portion of a circumference of said outer housing;
    said screw comprising a threaded screw shaft and a superiorly positioned screw head, said screw head being generally spherical;
    an articulation recess that is defined in the lower portion of said inner housing, said articulation recess being of complementary size and configuration to retain said screw head within said inner housing while allowing said screw head to be capable of rotation within said articulation recess;
    a screw shaft exit portal, which is defined by said inner housing at the lowest portion of said articulation recess sized to retain said screw head within said articulation recess while being of sufficient size to allow multi-planar rotational articulation of the screw head and the screw shaft exiting from said articulation recess;
    an inner housing connecting rod slot defined in the upper portion of said inner housing, said inner housing connecting rod slot being sized and configured to allow free movement of a connecting rod into and out of said inner housing slot and being configured such that a compressive force on said inner housing can effect a releasable locking contact of said inner housing connecting rod slot against a connecting rod positioned therein;

an outer housing connecting rod slot defined in the upper portion of said outer housing, said outer housing connecting rod slot being in alignment with said inner housing connecting rod slot and being of a size that permits a connecting rod to move freely within said outer housing connecting rod slot;

said inner housing and said outer housing having a generally complementary tapered shape for the respective opposing surfaces such that as said outer housing is slidably moved in an upward direction relative to said inner housing, said outer housing contacts said inner housing so as to be capable of producing a compressive force on the portion of the inner housing so contacted by said outer housing;

wherein said compressive force is sufficient to be capable of compressing said inner housing against said spherical screw head contained within said screw head recess and said connecting rod contained within said inner housing connecting rod slot so as to releasably hold said screw head and said connecting rod in a fixed position relative to said inner housing.

6. The screw according to claim 5, wherein said inner housing comprises at least one interior surface positioned in opposition to and adjacent to at least a portion of said spherical screw head.

7. The screw according to claim 6, wherein said at least one interior surface includes at least one surface positioned adjacent the upper portion of said spherical screw head and at least one surface positioned adjacent to the lower portion of said spherical screw head.

8. The screw according to claim 5, wherein said upper portion of said inner housing further comprises at least one connecting rod contact surface.

9. The screw according to claim 8, wherein said at least one connecting rod contact surface is at least one connecting rod upper contact surface positioned adjacent the position occupied by a connecting rod transversely positioned within said inner housing connecting rod slot and at least one connecting rod lower contact surface positioned adjacent to the position occupied by a connecting rod transversely positioned within said inner housing connecting rod slot.

10. The screw according to claim 9, wherein said articulation recess comprises at least one upper and one lower spherical head contact surface positioned adjacent an upper and lower portion of said spherical screw head respectively.

11. The screw according to claim 10, wherein said outer housing is capable of being slidably positioned in a full up and locked position relative to said inner housing, wherein said outer housing is contacting said inner housing with sufficient compressive force to force said connecting rod contact surfaces and said screw head contact surfaces of said inner housing to contact and securely fix said connecting rod and said screw head in their respective positions relative to said inner housing.

12. The screw according to claim 10, wherein said outer housing is capable of being slidably positioned in a full down and unlocked, open position relative to said inner housing, wherein said compressive contact between said outer housing and said inner housing is relieved or minimized such that said connecting rod is free to be moved within said inner housing connecting rod slot or removed from said inner housing connecting rod slot and said screw head is free to articulate within said articulation recess of said inner housing.

13. The screw according to claim 10, wherein said outer housing is capable of being slidably positioned into a fully locked position wherein said connecting rod and said spherical head are releasably locked in a relative position to said inner housing, and said outer housing is capable of being slidably positioned into a fully open position wherein said connecting rod and said spherical head can freely move relative to said inner housing, and said outer housing is capable of being slidably positioned to intermediary or partial locked position, wherein said outer housing exerts compressive forces on said inner housing sufficient to lock said spherical head in position relative to said inner housing and compressive forces exerted by said outer housing on the upper portion of said inner housing are relieved such that movement of said connecting rod within said inner housing connecting rod slot is possible.

14. The screw according to claim 5, wherein said outer housing also comprises opposing inner housing access slots that are defined through the opposing walls of said outer housing, said inner housing access slot being sized and configured to allow access for a complementarily configured unlocking tool, grasping elements of which are sized and configured to pass through said inner housing access slots and make grasping contact with a respective inner housing tool receptor that is accessible through said inner housing access slots, whereby said inner housing can be grasped by said tool and moved in relation to said outer housing from a locked position to a partially locked position or further moved to a fully unlocked position.

15. A kit for fixing bone, the kit comprising:
at one multi-planar screw according to claim 5, and
at least one connecting rod.

16. The kit according to claim 15, further comprising:
at least one tool configured to facilitate insertion of connection of said multi-planar screw and said connecting rod to bone.

17. The screw according to claim 5, wherein said inner housing connecting rod slot and said outer housing connecting rod slot define a longitudinal axis therealong that is transverse to a longitudinal axis of said screw shaft.

18. The screw according to claim 5, wherein said screw inner housing and said screw outer housing are permanently operably coupled.

19. The screw according to claim 5, wherein the annular flange extends from said screw outer housing at a downward angle, the annular flange being generally transverse to said common longitudinal axis of said inner and outer housings.

20. The multi-planar taper lock screw of claim 5, wherein at least a portion of said outer housing intersects a plane extending laterally from a central longitudinal axis defined through said connecting rod, the central longitudinal axis being transverse to said common longitudinal axis of said inner housing and outer housing.

* * * * *